United States Patent [19]

Kissinger

[11] Patent Number: 4,876,391
[45] Date of Patent: Oct. 24, 1989

[54] PROCESS FOR PREPARATION AND PURIFICATION OF BISPHENOLS

[75] Inventor: Gaylord M. Kissinger, Evansville, Ind.

[73] Assignee: General Electric Company, Mt. Vernon, Ind.

[21] Appl. No.: 244,370

[22] Filed: Sep. 15, 1988

[51] Int. Cl.$^4$ .................. C07C 37/68; C07C 37/86; C07C 39/16
[52] U.S. Cl. .................................. 568/724; 568/727
[58] Field of Search ........................... 568/724, 727

[56] References Cited

U.S. PATENT DOCUMENTS

| 4,330,664 | 5/1982 | Brunnelle | 528/198 |
|---|---|---|---|
| 4,345,062 | 8/1982 | Brunnelle | 528/198 |
| 4,443,635 | 4/1984 | McLaughlin | 568/724 |
| 4,590,257 | 5/1986 | Brunnelle | 528/176 |

FOREIGN PATENT DOCUMENTS 0115733  9/1981  Japan ................................. 568/724

*Primary Examiner*—Werren B. Lone
*Attorney, Agent, or Firm*—Martin B. Barancik

[57] ABSTRACT

A process which comprises
(a) contacting an excess of a phenol with a ketone in the presence of an acidic ion exchange resin catalyst;
(b) recovering thereafter a stream from the acidic ion exchange resin catalyst including the dihydric phenol, unreacted phenol, isomers of the desired dihydric phenol and acid impurities derived from the acidic ion exchange resin catalyst;
(c) removing a major portion of the desired dihydric phenol from the stream of (b);
(d) separating the stream including phenol, a small portion of the desired dihydric phenol, isomers of the desired dihydric phenol, and acidic impurities derived from the acidic ion exchange resin catalyst into a major stream and a minor stream by volume;
(e) introducing into the minor stream created at step (d) sufficient quantities of a tetraorganoammonium borohydride to effectively neutralize the acidic impurities derived from the acidic ion exchange resin catalyst; and
(f) recovering from the minor stream desirable dihydric phenol.

6 Claims, No Drawings

PROCESS FOR PREPARATION AND PURIFICATION OF BISPHENOLS

BACKGROUND OF THE INVENTION

The dihydric phenols have achieved significant success in their commercial applications. Dihydric phenols are useful in the commercial manufacture of various polymers including the polyarylates, polyamides, epoxies, polyetherimides, polysulfones and the polycarbonates. Significant attention has been directed to the commercial preparations of the dihydric phenols. For many years it has been well known that the acid catalyzed reaction of phenol with specific aldehyde or ketone could prepare the 4,4'-dihydric phenol with specific groups derived from the aldehyde or the ketone connecting the two phenolic rings. In particular when phenol is reacted with acetone, the dihydric phenol, 4,4'(hydroxyphenyl)propane-2, hereafter known as bisphenol-A is formed. This has particular utility in polycarbonates, polyarylates and copolyestercarbonates as well as epoxies. In order to make certain polymers, in particular the polycarbonates, the bisphenol-A must be particularly pure, for example, as measured by color. Additionally, the process should be particularly efficient since the dihydric phenol costs contribute substantially to the cost of the final polymer. Therefore much attention has been directed to the recovery of biphenol-A after preparation. Not only is recovery from the major stream containing primarily bisphenol-A important, but because of the economics involved, various side streams or "purge streams" also containing significant quantities of bisphenol-A should also be investigated for improved recovery economics.

Various catalytic systems for acid catalysis of the reaction between phenol and bisphenol-A have been investigated and used commercially. At one time the hydrochloric acid catalyzed process was used in a significant number of commercial facilities. However the corrosion caused by the hydrochloric acid on standard metallic reactors and pre and post reaction equipment left much to be desired as far as replacement economies was concerned. Recently, substantial attention has been placed on using an ion exchange resin catalyst system since it does not have a significant acid corrosion problem. However it has recently been discovered in our equipment that the usual processing techniques for recovery of bisphenol-A from recovery streams having relatively small amounts of bisphenol-A, about 6 to 15 weight percent of the process stream, after preparation with the ion exchange catalyst cannot be practiced in the same manner as when using the hydrochloric acid catalyst system. Substantial quantities of bisphenol-A which could be isolated from streams having a major quantity of phenol after reaction with an HCl catalyzed system could no longer be recovered when using an ion exchange system. Additionally the quality of the bisphenol-A which could be recovered as well as the quality of other materials in these "purge streams" was sufficiently lessened as measured by the color of the materials. Color is a very important property of the final polymers which are prepared from the bisphenol-A as well as the bisphenol-A itself. For example, bisphenol-A polycarbonate is known to be clear and colorless.

It has now been discovered that bisphenol-A can be successfully recovered in substantial quantities from the purge streams of an ion exchange catalyzed reaction of a phenol with a ketone, particularly phenol per se with acetone, by utilizing a relatively simple treatment with a specific system. Not only is the dihydric phenol recoverable from the purge streams, but the color of the dihydric phenol and the recyclable components is substantially improved.

SUMMARY OF THE INVENTION

In accordance with the invention, there is a process which comprises (a) contacting an excess of a phenol with a ketone in the presence of an acidic ion exchange resin catalyst;

(b) recovering thereafter a stream from an acidic ion exchange resin catalyst, said stream including the dihydric phenol, unreacted phenol, isomers of the desired dihydric phenol and acid impurities derived from the acidic ion exchange resin catalyst;

(c) removing a major portion of the desired dihydric phenol from the stream of (b);

(d) separating the stream including phenol, a small portion of the desired dihydric phenol, isomers of the desired dihydric phenol, and acidic impurities derived from the acidic ion exchange resin catalyst into a major stream and a minor stream by volume;

(e) introducing into the minor stream created at (d) sufficient quantities of a tetra organo ammonium borohydride to effectively offset the acidic impurities derived from the acidic ion exchange resin catalyst; and (f) recovering from the minor stream desirable dihydric phenol.

In further accordance with the invention there is a process for preparing and isolating a dihydric phenol from the reaction of a phenol and a ketone in the presence of an acidic ion exchange resin catalyst, the improvement comprising the addition to the process of sufficient quantities of tetraorganoammonium borohydride to a minor portion of the split process stream created after the removal from the stream of a major quantity of the desired dihydric phenol to effectively offset acidic impurities provided from the acidic ion exchange resin catalyst, said impurities carried with the desired dihydric phenol in the downstream processing steps from the catalyst.

DETAILED DESCRIPTION OF THE INVENTION

The most well known dihydric phenol is bisphenol-A. The invention shall be further described in detail with the production of bisphenol-A. However, any other dihydric phenol is anticipated to have these problems if made from the reaction of a phenol with an acetone and an acidic ion exchange resin catalyst system which has produced acidic impurities.

Phenol and acetone are passed into a reactor having an acidic ion exchange resin catalyst system. Such catalyst system is usuablly an Amberlite type resin obtained from Rohm and Haas. This resin has a styrenic backbone with pendant $SO_3H$ groups which provide the acidic character to the resin. Usually the styrene is crosslinked with a small quantity of divinyl benzene or other crosslinking chemical. This addition of a crosslinker appears to provide structural strength and rigidity to the catalyst. The phenol in excess, together with the acetone, is passed over the acidic ion exchange resin. Other ion exchange resins can also be used although it is preferable to use the styrenic backbone crosslinked with the difunctional monomer and having SO₃H groups pendant from the aromatic nucleus of the styrene moiety.

The stream coming off the catalyst has the bisphenol-A, excess phenol, isomers of bisphenol-A, isopropenyl phenol (IPP), chromans (which are addition products of various bisphenols), spiro biindanes and other side reaction products of the reaction of the phenol with the acetone. Additionally present in the stream coming off the ion exchange resin was the unrealized formation of acidic impurities derived from the acidic ion exchange resin. Although not to be held by this theory of the invention, it is believed that acidic ion exchange resins may not be fully polymerized and that held within the network of the solid resin are acidic impurities, perhaps of an oligomeric nature. When such resins are contacted with appropriate reactants and products, such oligomeric acidic impurities can be leached therefrom and join the product stream. At various points within the downstream processing such acidic impurities may build up to such an extent that they catalyze undesired reactions between the materials present in the stream.

At this point a substantial amount of the bisphenol-A is removed from the stream. Bisphenol-A is unlike other dihydric phenols in that it forms a stable addition adduct with phenol. This physical addition adduct is utilized in the removal of the bisphenol-A from the stream. Various recovery processes are then utilized to separate the bisphenol-A from the phenol, finally producing a high quality bisphenol-A. The mother liquor from the bisphenol-A phenol adduct has a substantial amount of phenol and a minor amount of bisphenol-A, isomers, IPP, chroman, spiro biindane, and the like.

In order to control the reaction kinetics and provide a balance between the color and side reaction products which can occur in the preparation of bisphenol-A from phenol and acetone, it is important to recycle a substantial portion of a stream having these types of components therein to the reactor which contains the reactants and catalysts system. The quantity of the stream which is recycled depends upon the level of color and side product reactions and impurities which one wishes to maintain or reduce in the actual reaction scheme. This stream can be the actual stream removed as mother liquor from the adduct or it can go through other purification steps which remove quantities of materials which are considered undesirable or which have specific high value and are therefore removed from the process at an early stage. Generally the quantity of material which is recycled to the reactor is from about 85 to about 93 volume percent of the stream. The smaller amount, that is the 7 to about 15 volume percent, is then usually processed to remove the high value contents therefrom. Obviously one of these is bisphenol-A. This was common practice in the hydrochloric acid catalyzed process for preparing bisphenol-A. However, when attempted with an acidic ion exchange resin catalyzed reaction product stream, little or no biphenol-A was found in the stream where significant quantitites were expected.

After a substantial amount of research and testing it was found that there was significant quantitites of acidic impurities present in the stream. It appears to be, although we do not wish to limit the invention to this particular theory, these impurities which cause the bisphenol-A to disappear. A postulated mechanism which may account for the disappearance of the bisphenol-A and the appearance of significant color bodies in the recycled material is the acid catalyzed breakdown of bisphenol-A to isopropenylphenol (IPP) and phenol.

The former material, IPP, is a highly colored substance.

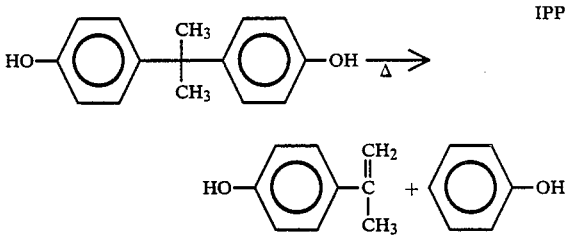

Once more, after substantial research it has now been found that the effects of the acid can be obviated by adding acid offset effective amounts of a tetraorganoammonium borohydride. Examples of such organo groups include aliphatic and aromatic groups. Examples of aliphatic groups include alkyl from one to twelve carbon atoms, inclusive, normal and branched, alkenyl of two to twelve carbon atoms, inclusive, normal and branched, cycloalkyl and cycloalkylene of five to seven carbon atoms inclusive. Aromatics include phenyl and mono to tri substituted alkyl phenyl wherein alkyl is one to three carbon atom, inclusive. Although not usually considered as organic group, hydrogen is also included. Although it is believed that the tetraorganoammonium borohydride compound accomplishes its effect by neutralizing the acidic impurities, it is not known that is the case.

The acid offsetting material is added to the minor stream of step (d) which is formed after the major quantity of dihydric phenol has been removed. In processing after the dihydric phenol has been removed from the stream, in particular bisphenol-A as a solid bisphenol-A phenol adduct, the "mother liquor" is then split into two streams, a major and a minor stream. The major stream, as mentioned previously, is recycled to the reaction. The minor stream is then processed for recovery of its constituent materials, including phenol and dihydric phenol. Since it is undesirable for the acid offsetting material to be in contact with the reactor resin, the acid offsetting material is added to this minor stream.

Further advantages of using the acid offsetting material are the compatibility with the dihydric phenol and the later formed polymer made therefrom. No adverse results upon color or further processing of the desired compositions have been observed with these materials. Additionally, upon combustion of the dihydric phenol or polymer, very little if any residue or ash content is traced to the acid offsetting agent as opposed to the use of a heavier metallic compound.

The quantity of acid offsetting material which may be present should be sufficient to recover as much as one would necessarily expect within experimental parameters of bisphenol-A from the minor stream of step (d). This obviously depends upon the quantity of acidic impurities which may be present in the stream and the efficiency of the contact of the acid offsetting material with the acidic impurities in the downstream processing equipment. Therefore, addition of acid offsetting material is monitored so that the acidic impurity is essentially titrated to zero or as close to zero as can be obtained. One should be observant about adding excess acid offsetting material since this has somewhat basic character and can also cause degradation of the desired dihydric phenol. In actual practice, this quantity will change depending upon the level of acidic impurities which are present. We have found that from about 5 to about 100 ppm of acid offsetting material calculated on the basis of the total stream weight is sufficient to bring about substantial recovery of the bisphenol-A from the minor stream.

Below are examples of the invention. These examples are intended to be illustrative of the scope of the invention and not to limit it therein.

In the examples below, P,P is bisphenol-A, IPP is isopropenyl phenol, O-P is the ortho-para isomer of bisphenol-A, "dimer" is IPP dimers, BPX-1 is a tris-phenol, CR-1 is chroman-1, "spiro" is spirobiindane, BPX-II is a further trisphenol.

In the examples below the following procedures were used. The bisphenol-A were prepared using phenol and acetone and condensing over a sulfonated polystyrene catalyst system. The bisphenol-A phenol adduct was formed and precipitated. The mother liquor was separated from the precipitated adduct. 400 grams of the mother liquor was put into a 1000 ml flask. On the control no additive was added. For the test materials a tetraorganoammonium borohydride was put into a separate 400 gram sample in a certain quantity. Liquid chromatographic analyses were run on the mother liquor starting material to quantify the various amounts of materials present in the mother liquor. A condensor was put into the flask, phenol was condensed from the flask until a temperature of 210° C. was reached. When this temperature was reached, water was put through the condensors to start refluxing. The remainder of the 400 gram sample was refluxed for four hours. After the four hours of refluxing, the material in the flask was then subject to a liquid chromatographic analysis once more. Below are the results of the experiments. All composition values are in grams. % loss refers to % loss in BPA from the starting composition. In the examples below the acid offsetting material was tetramethylammonium borohydride (TMABH) in the stated ppm quantities.

EXAMPLE 1

|  | START | CONTROL | TMABH ppm | | |
|---|---|---|---|---|---|
|  |  |  | 10 | 20 | 50 |
| Start temp |  | 210 | 210 | 210 | 210 |
| End temp |  | 206 | 209 | 208 | 207 |
| Bottom |  | 63.9 | 70.44 | 78.45 | 77.48 |
| OOH | 346.0 | 24.0 | 26.0 | 28.0 | 27.2 |
| P.P | 30.16 | 21.7 | 27.68 | 29.5 | 28.3 |
| O.P | 7.52 | 3.7 | 5.7 | 7.2 | 7.3 |
| Dimer | 5.3 | 4.3 | 4.1 | 5.35 | 5.4 |
| BPX-I | 1.81 | 1.42 | 1.4 | 1.73 | 2.0 |
| CR-1 | 1.87 | 1.45 | 1.5 | 1.91 | 1.9 |
| Spiro | .252 | .252 | .80 | 1.0 | .775 |
| BPX-II | .872 | 1.48 | .70 | .84 | .821 |
| IPP | NDA | .349 | .200 | .426 | .763 |
| % Loss |  | 28.0 | 8.2 | 2.1 | 6.16 |

As shown by the data the addition of TMABH brings about a substantial reduction in the loss of bisphenol-A. As shown a smaller amount of TMABH (10 ppm) does not lower the loss of bisphenol-A as much as an amount closer to the titration figure (20 ppm). However, significantly beyond the titration will also raise the quantity of loss beyond the minimum because the TMABH is possibly acting in a basic manner, thereby behaving as a basic catalyst and enhancing cracking of bisphenol-A.

EXAMPLE 2

| A. | | | |
|---|---|---|---|
|  | START | CONTROL | TMABH 20 ppm |
| Start temp |  | 210 C | 210 C |
| End temp |  | 204 C | 210 C |
| Bottom |  | 96.7 G | 104.5 |
| OOH | 335.6 | 39.0 | 39.8 |
| P.P | 34.1 | 27.3 | 33.9 |
| O.P | 10.1 | 6.0 | 9.5 |
| Dimer | 7.2 | 6.9 | 7.1 |
| BPX-I | 2.34 | 1.9 | 2.3 |
| CR-1 | 3.59 | 3.4 | 3.6 |
| Spiro | .356 | .527 | .377 |
| BPX-II | 1.7 | 3.17 | 1.7 |
| IPP | .004 | .571 | .611 |
| % Loss |  | 21.0 | 0.6 |

| B. | | | |
|---|---|---|---|
|  | START | CONTROL | TMABH 50 ppm |
| Start temp |  | 210 | 210 |
| End temp |  | 203 | 209 |
| Bottom |  | 98.5 | 106.5 |
| OOH | 332.0 | 40.0 | 40.0 |
| P.P | 36.2 | 26.4 | 33.8 |
| O.P | 10.1 | 5.4 | 9.7 |
| Dimer | 7.44 | 7.44 | 7.6 |
| BPX-I | 2.46 | 1.8 | 2.42 |
| CR-1 | 3.96 | 3.67 | 3.99 |
| Spiro | .376 | .384 | .356 |
| BPX-II | 2.27 | 3.43 | 1.76 |
| IPP | NDA | .452 | .910 |
| % Loss |  | 27.0 | 6.6 |

| C. | | | |
|---|---|---|---|
|  | START | CONTROL | TMABH 1000 ppm |
| Start temp |  | 210 | 210 |
| End temp |  | 203 | 206 |
| Bottom |  | 98.0 | 103.7 |
| OOH | 336.0 | 41.0 | 41.9 |
| P.P | 35.6 | 29.4 | 31.0 |
| O.P | 9.6 | 5.9 | 8.87 |
| Dimer | 5.9 | 5.9 | 5.9 |
| BPX-I | 2.5 | 2.2 | 4.98 |
| CR-1 | 3.5 | 2.7 | 3.3 |
| Spiro | .368 | .572 | .682 |
| BPX-II | 1.72 | 3.2 | 2.3 |
| IPP | NDA | .54 | .761 |
| % Loss |  | 18.0 | 13.0 |

The same observations from Example 1 are pertinent here. The higher in ppm TMABH one goes beyond the minimum, the more bisphenol-A is lost.

As shown in all the examples, the addition of the acid offsetting material brought about a substantial reduction in lost BPA in comparison to the samples not treated with the material.

What is claimed is:

1. A process which comprises
   (a) contacting an excess of phenol with acetone in the presence of an acidic ion exchange resin catalyst;
   (b) recovering thereafter a stream from the acidic ion exchange resin catalyst including bisphenol-A, unreacted phenol, isomer of bisphenol-A and acid impurities derived from the acidic ion exchange resin catalyst;
   (c) removing a major portion of bisphenol-A from the stream of (b);
   (d) separating the stream including phenol, a small portion of bisphenol-A, isomers of bisphenol-A, and acidic impurities derived from the acidic ion exchange resin catalyst into a major stream and a minor stream by volume;

(e) introducing into the minor stream created at step (d) sufficient quantities of a tetraorganoammonium borohydride to effectively offset the acidic impurities derived from the acidic ion exchange resin catalyst; and (f) recovering from the small stream desirable dihydric phenol.

2. The process in accordance with claim 1 wherein the organo groups are the same and are methyl.

3. The process in accordance with claim 1 wherein the organo groups are the same and are phenyl.

4. In a process for preparing a dihydric phenol from the reaction of phenol and acetone in the presence of an acidic ion exchange resin catalyst, the improvement comprising the addition to the process of sufficient quantities of a tetraorganoammonium borohydride to a minor portion of the split process stream created after the removal from the stream of a major quantity of bisphenol-A to effectively offset acidic impurities provided from the acidic ion exchange resin catalyst, said impurities carried with bisphenol-A in the downstream processing steps from the catalyst.

5. The process in accordance with claim 4 wherein the organo groups are the same and are methyl.

6. The process in accordance with claim 5 wherein the organo groups are the same and are phenyl.

* * * * *

UNITED STATES PATENT AND TRADEMARK OFFICE
CERTIFICATE OF CORRECTION

PATENT NO. : 4,876,391

DATED : October 24, 1989

INVENTOR(S) : Gaylord Michael Kissinger

It is certified that error appears in the above-identified patent and that said Letters Patent is hereby corrected as shown below:

Col.1, line 28
Delete "biphenol-" and add "bisphenol-"

Col.3, line 57
Delete "biphenol-A" and add "bisphenol-A"

Col.7, line 6
Delete "desirable dihy-"

Col.7, line 6
After "stream" add "bisphenol-A"

Col.7, line 7
Delete "dric phenol"

Col.7, line 12
Delete "a dihydric phenol" and add "bisphenol-A"

Signed and Sealed this

Twenty-third Day of October, 1990

Attest:

HARRY F. MANBECK, JR.

*Attesting Officer*     *Commissioner of Patents and Trademarks*